United States Patent
Bödewadt et al.

(10) Patent No.: US 10,463,376 B2
(45) Date of Patent: Nov. 5, 2019

(54) IMPLANTABLE MEDICAL DEVICE WITH FLEXIBLE CONNECTION

(71) Applicant: COOK MEDICAL TECHNOLOGIES LLC, Bloomington, IN (US)

(72) Inventors: Tue Thuren Bödewadt, Solroed Strand (DK); Christina Rauff Hansen, Valby (DK)

(73) Assignee: Cook Medical Technologies LLC, Bloomington, IN (US)

( * ) Notice: Subject to any disclaimer, the term of this patent is extended or adjusted under 35 U.S.C. 154(b) by 462 days.

(21) Appl. No.: 14/593,545

(22) Filed: Jan. 9, 2015

(65) Prior Publication Data
US 2015/0196301 A1    Jul. 16, 2015

(30) Foreign Application Priority Data
Jan. 10, 2014    (GB) .................................. 1400391.7

(51) Int. Cl.
*A61B 17/12*    (2006.01)
*A61F 2/01*    (2006.01)

(52) U.S. Cl.
CPC .... *A61B 17/12036* (2013.01); *A61B 17/1215* (2013.01); *A61B 17/12109* (2013.01); *A61B 17/12145* (2013.01); *A61F 2/01* (2013.01); *A61F 2002/016* (2013.01); *A61F 2210/0014* (2013.01); *A61F 2230/0023* (2013.01); *A61F 2230/0078* (2013.01); *A61F 2250/0039* (2013.01)

(58) Field of Classification Search
CPC ........... A61B 2017/00575; A61B 2017/00606; A61B 17/12036; A61B 17/1215
See application file for complete search history.

(56) References Cited

U.S. PATENT DOCUMENTS 5,370,657 A    12/1994 Irie
5,683,411 A    11/1997 Kavteladze et al.
(Continued)

FOREIGN PATENT DOCUMENTS

DE    10 2005 032308 A1    1/2007
WO    WO 99/07292 A1    2/1999
(Continued)

OTHER PUBLICATIONS

Extended Search Report for European Patent Application Serial No. 14275260.9 dated May 8, 2015, 5 pages.
(Continued)

*Primary Examiner* — Thomas M McEvoy
(74) *Attorney, Agent, or Firm* — Brinks Gilson & Lione

(57) ABSTRACT

An implantable medical device includes first and second material capture elements which are disposed in opposing orientations and have their narrow ends facing one another. The first and second material capture elements are connected by a flexible connector, which enables the implantable medical device to curve within a curved vessel of a patient. The flexible connector is either closed or has a lumen passing therethrough and includes a closure element for closing the lumen after deployment of the device within a patient. The structure enables the device to be positioned reliably within a curved vessel and benefits from the advantage of a double-ended device.

13 Claims, 5 Drawing Sheets

(56) References Cited

U.S. PATENT DOCUMENTS

| | | |
|---|---|---|
| 6,117,157 A | 9/2000 | Tekulve |
| 6,419,686 B1 | 7/2002 | McLeod et al. |
| 2003/0153935 A1 | 8/2003 | Mialhe |
| 2006/0058820 A1* | 3/2006 | Mialhe ............... A61B 17/0057 606/157 |
| 2006/0136043 A1 | 6/2006 | Cully et al. |
| 2007/0073337 A1* | 3/2007 | Abbott ............... A61B 17/0057 606/213 |
| 2008/0051830 A1 | 2/2008 | Eidenschink et al. |
| 2009/0177221 A1 | 7/2009 | Kramann |
| 2010/0163054 A1 | 7/2010 | Breznel et al. |
| 2011/0144689 A1 | 6/2011 | Isch et al. |
| 2011/0184439 A1* | 7/2011 | Anderson .......... A61B 17/0057 606/151 |
| 2015/0005810 A1* | 1/2015 | Center ..................... A61F 2/01 606/200 |

FOREIGN PATENT DOCUMENTS

| | | |
|---|---|---|
| WO | WO 02/19926 A1 | 3/2002 |
| WO | WO 2003/028522 | 4/2003 |
| WO | WO 2009/124247 A2 | 10/2009 |
| WO | WO 2012/092377 | 7/2012 |

OTHER PUBLICATIONS

Examination Report for GB Application No. GB1400391.7 (dated Feb. 11, 2015).
Examination Report for GB Application No. GB1400391.7 (dated Aug. 11, 2014).

\* cited by examiner

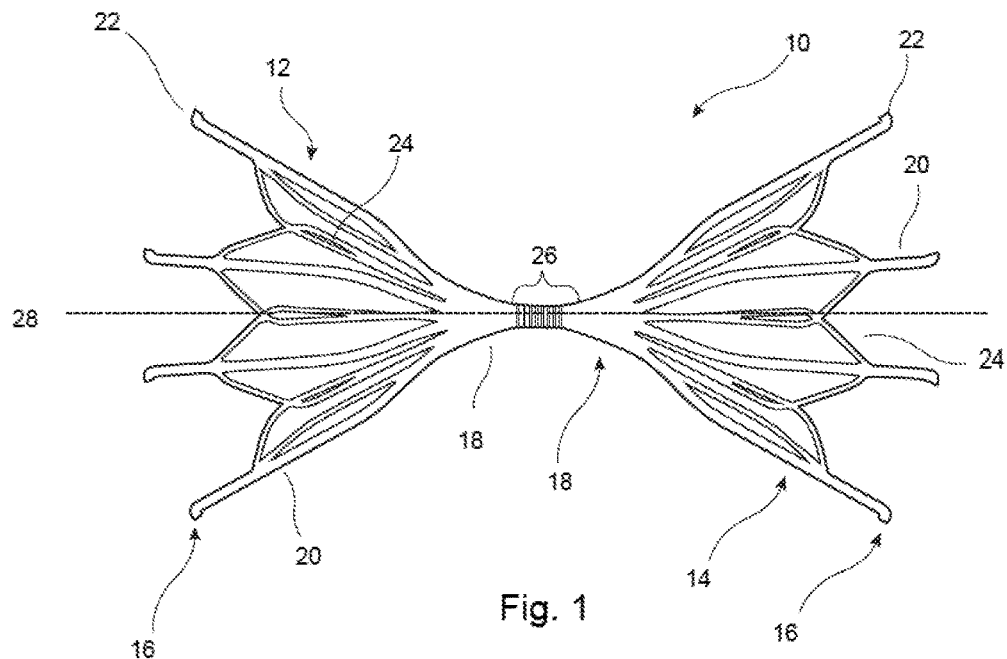
Fig. 1
Fig. 2
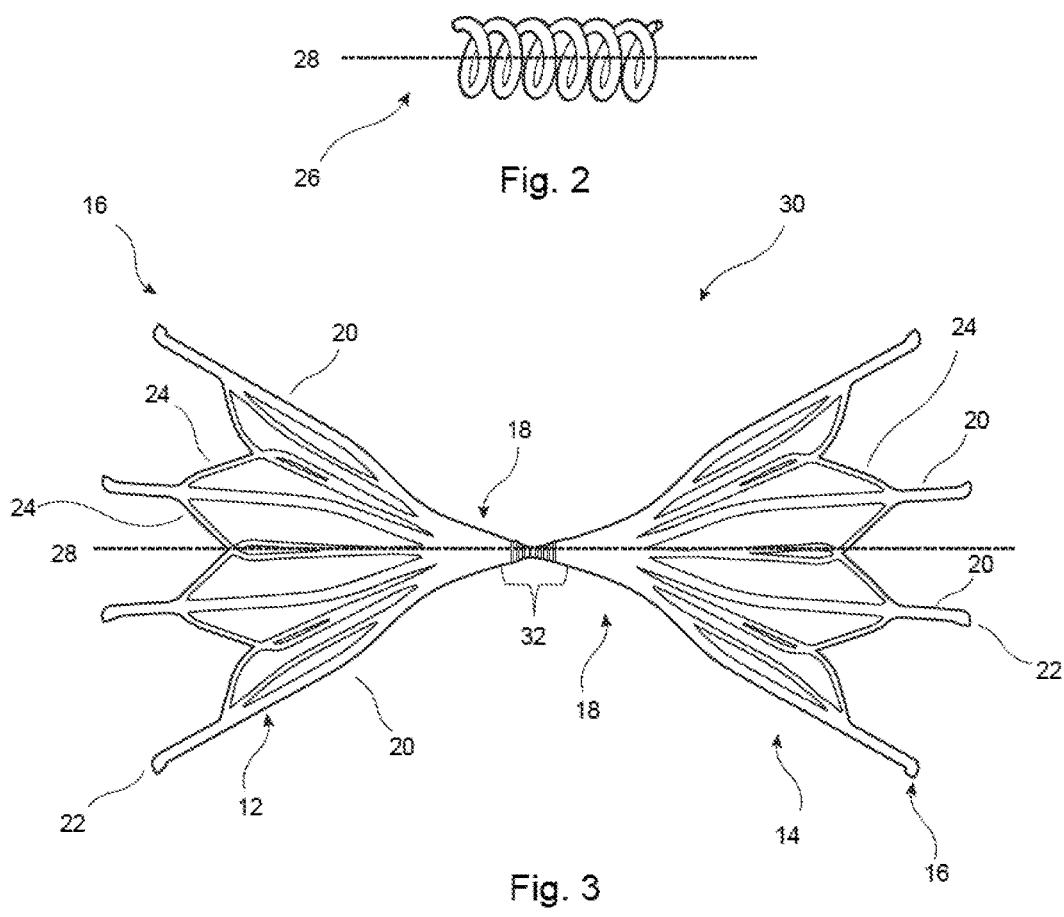
Fig. 3

IMPLANTABLE MEDICAL DEVICE WITH FLEXIBLE CONNECTION

CROSS-REFERENCE TO RELATED APPLICATIONS

This application claims the benefit of priority under 35 U.S.C. § 119(a) to Great Britain Patent Application No. 1400391.7, filed Jan. 10, 2014, which is incorporated by reference here in its entirety.

Technical Field

The present invention relates to an implantable medical device, in the described embodiments to a filter or occluder.

Background Art

Implantable filters and occluders have been known for some years. Some are single ended and may have a conical or part conical form. While such a form can effectively trap material within the cone, the device can suffer from misalignment and migration problems in vivo. Moreover, these types of device can only be disposed in one orientation in a patient and often can only be retrieved for removal from a single direction.

Other types of device are double ended and may for instance be formed of two conical or part conical elements disposed in opposing relationship and connected together at their adjoining narrow ends, either directly or by a suitable rod or cannula. A double ended device can be implanted in either orientation in a patient's vessel. The structure provides for a more stable device which can have better positional and migration resistance compared to a single ended device. However, double ended devices can be less suitable for deployment in curved lumens as they tend to maintain a substantially straight configuration.

Examples of some known filters and occluders can be found in U.S. Pat. Nos. 6,419,686, 5,370,657, US-2010/163,054 and WO-2012/092,377.

SUMMARY OF THE INVENTION

The present invention seeks to provide an improved implantable medical device and in the preferred embodiments an improved filter or occluder.

According to an aspect of the present invention, there is provided an implantable medical device including: first and second material capture elements each having a wide end and a narrow end, the first and second material capture elements being disposed with their narrow ends facing one another and their wide ends extending in opposing directions; a flexible connecting element connected to the narrow ends of the first and second material capture elements to form a unitary device with the first and second material capture elements; the flexible connecting element being one of closed and closable to passage of fluid therethrough.

The structure is double ended, therefore having the advantages of a double ended device, and is provided with a flexible coupling between the two material capture elements, which enables the device to follow the curve of a vessel without imparting unnecessary straightening forces on the vessel.

In a preferred embodiment, the connecting element is a coil, the coil providing a lumen therewithin, there being provided a closure element to close passage of fluid through the coil. More specifically, the connecting element may be a coiled wire or a helically cut cannula.

The provision of a coil or cannula enables the device to be delivered over a guide wire, which considerably facilitates the deployment of the device compared to prior art devices.

Advantageously, the closure element is a valve, the valve being openable to allow passage through the lumen of the coil and closable to block passage through the lumen. The valve may be in the form of an openable and closable barrier. In one embodiment, the closure element is formed of silicone.

The provision of such a closure element ensures closure of the lumen in the coil or cannula after deployment, thereby ensuring that there is no blood or debris loss through the centre of the device.

In an embodiment, the closure element is disposed within the lumen of the coil. In another embodiment, the closure element is disposed in one of the first and second material capture elements. There may be provided a second closure element disposed in the other of the first and second material capture elements.

In another embodiment, the closure element is constituted by a portion of the coil which is a narrow waist closing the lumen therein. The waist is preferably openable by twisting, whereby the closure element can act as a valve allowing passage through the lumen when open and blocking passage through the lumen when closed.

In another embodiment, the closure element is in the form of thrombogenic fibres disposed so as to extend across the lumen of the coil.

A combination of such closure elements may be used if desired.

Another embodiment provides for the connecting element to be a rod having transversally extending grooves, channels or recesses. The slits give the rod flexibility to bend without significant resistance.

In another embodiment, the connecting element is a rod of flexible material.

Advantageously, the first and second material capture elements each include a frame, the connecting element being attached to the frame. The frames of the first and second material capture elements may be one piece with the connecting element.

The frames of the first and second material capture elements and the connecting element may be made of shape memory alloy.

In one embodiment, the device is an occluder and the material capture elements are impervious to fluid. In another embodiment, the device is a filter and the material capture elements are fluid porous.

Other features and advantages will become apparent form the following specific description and accompanying drawings.

BRIEF DESCRIPTION OF THE DRAWINGS

Embodiments of the present invention are described below, by way of example only, with reference to the accompanying drawings, in which:

FIG. 1 is a schematic diagram in side elevation of an embodiment of filter;

FIG. 2 is an enlarged view of the flexible connecting element of the filter of FIG. 1;

FIG. 3 is a schematic diagram in side elevation of another embodiment of filter;

DESCRIPTION OF THE PREFERRED EMBODIMENTS

Figure 4:
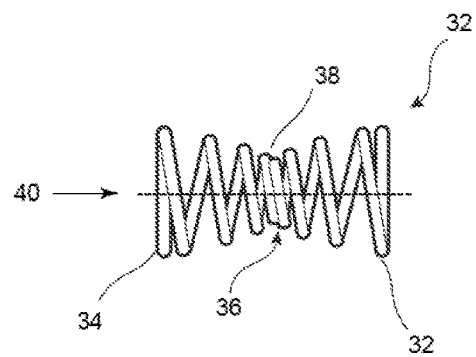
FIG. 4 is an enlarged view of a flexible connecting element having a waist, of the filter of FIG. 3.

Various embodiments of filter assembly or structure are disclosed below and in the accompanying drawings. It is to be understood that the teachings herein are not limited to filters and apply equally to occluders and other implantable medical devices.

The medical device is of a double ended type and is preferably symmetrical about its centre point, such that it can be used in either orientation in a patient's vessel. By symmetrical, it is preferred that the two sides of the device are identical to one another but facing opposite directions, although in some embodiments the device may not be symmetrical and each side may have different characteristics, dimensions and/or functions.

Referring first to FIG. 1, this shows in side elevation a first embodiment of implantable medical device 10, which is configured as a filter. The filter 10 is provided with first and second filter baskets 12, 14, otherwise termed material capture elements, each of which has a wide end 16 and a narrow end 18. Each filter basket 12, 14 in this embodiment could be said to have a generally conical form. In this example, each filter basket 12, 14 has a plurality of legs 20 which terminate with barbed ends 22, of known form. Intermediate struts 24 extend into the spaces between the legs 20, so as to provide a frame having apertures small enough to trap debris within a patient's vessel, yet large enough to allow the flow of fluid therethrough and in particular bold plasma.

Each filter basket 12, 14 can be cut from a cannula, for example by laser cutting, and by bending back the ends to form the barbs 22. The baskets 12, 14 can in other embodiments be manufactured from separate components which are then welded, soldered, bonded or otherwise attached together.

In this embodiment, it is preferred that the narrow end 18 of each filter basket 12, 14 is not completely closed but provides a lumen therethrough for the passage of a guide wire (not shown).

Disposed between the filter baskets 12, 14 is a flexible connecting element 26 which is attached to or integral with each narrow end 18 of the respective baskets 12, 14, so as to create a structure which could be described as having an hourglass shape. In the embodiments shown, the flexible connecting element 26 has a lumen passing therethrough, such that there is a continuous and uninterrupted lumen or channel passing through the centre of the device 10, indicated by the dotted line 28 in the Figures.

The flexible connecting element forms a unitary device with the first and second filter baskets 12, 14 and for this for this purpose may be welded, soldered, bonded or otherwise attached to the filter baskets 12, 14. In some embodiments, the flexible connecting element can be formed with the filter baskets 12, 14 from a single tubular blank, for instance by laser cutting.

It is preferred that the flexible connecting element 26 has a relatively short length, preferably in the region of 1 to 5 millimeters, with an inner diameter of around 0.6 millimeters (2 French) to around 2 millimeters (6 French) or even larger, and an outer diameter of around 0.9 millimeters to around 3 millimeters. The flexible connecting element 26, therefore, does not unduly increase the overall length of the implantable medical device 10.

As is described in further detail below and shown in the accompanying drawings, the flexible connecting element 26 is closable to the passage of fluid therethrough. This may be achieved in a variety of ways, as described hereinafter.

Referring to FIG. 2, in the embodiment of FIG. 1, the flexible connecting element 26 is in the form of a coil of wire, which could be said to have characteristics similar to those of a coil spring. It is preferred that the coil 26 is relatively flexible, in particular to have a low restoring force in a bending direction. Specifically, it is preferred that the force the coil generates when deflected from its straight configuration is substantially less than the strength of the walls of a vessel within which the device 10 is to be implanted. The connecting element 26 will as a result remain curved in a curved vessel without forcing the vessel to straighten, as can occur with relatively rigid implantable medical devices. In the preferred embodiments the connecting element 26 is such as to minimize the effect of the filter or other medical device on the vessel walls, in particular when the device is implanted in a curved vessel.

The embodiment of flexible connecting element 26 shown in FIG. 2 is formed from a coiled wire in which the wire has a substantially circular cross-section. Other embodiments have a coil formed from a strip of material, with the wide part of the strip extending in the longitudinal direction of the flexible connecting element. Another embodiment creates an analogous device by helically cutting a cannula.

It is preferred in all embodiments that the turns of the coil are as close to one another as possible to leave the smallest and preferably no substantial gap between each turn.

In the embodiment of FIGS. 1 and 2, the flexible connecting element 26 is substantially cylindrical, that is each turn of the coil has substantially the same diameter as the other turns. In this embodiment, as described below, there is provided a closure element to close the lumen 28 extending through the flexible connecting element 26. Examples of closure elements are described below.

FIG. 1, as described above, is directed to an implantable filter but it is to be understood that the relevant parts of this structure, in particular of the flexible connecting element, can be applied to other medical devices such as occluders and so on. An occluder can be formed, for example, by attaching an impervious covering to the filter baskets 12, 14, made of any suitable material. Examples include: ultrahigh molecular weight polyethylene such as Dyneema, polyethylene terephthalate such as Dacron, polyamide such as Nylon and any other material commonly used for grafts.

Referring now to FIGS. 3 and 4, these show another embodiment of filter 30, which has a general structure the same as that of the embodiment of FIG. 1, that is with generally conical filter baskets 12, 14 arranged in opposing relation, that is also in an hourglass configuration.

This embodiment includes a flexible connecting element 32 connecting the narrow ends 18 of the baskets 12, 14 and is attached to or is otherwise integral with the baskets 12, 14 in the manner described above.

As will be apparent from FIG. 4, the flexible connecting element 32 of this embodiment is formed of a coil having larger coil turns 34 at its ends and a waist 36 formed by coil turns 38 of a smaller diameter. It is preferred that the coil turns decrease gradually from the extremities 34 to the centre point 38, so as to have what could be described as a double taper or an hourglass shape. It is preferred that the turns 34, 38 of the coil 32 are tight against one another in a longitudinal direction of the element 32. The coil 32 can, as with the embodiment of FIGS. 1 and 2, be formed of a wire, strip or laser cut from a cannula.

The arrangement of FIGS. 3 and 4 is therefore similar to the embodiment of FIGS. 1 and 2, save for the fact that the waist 36 of the connecting element 32 increases the flexibility of the connecting element and therefore the ease with which the device can be made to curve, as is explained in further detail below. Moreover, the waist 36 narrows the diameter of the lumen 40 passing through the flexible connecting element 32, preferably to such an extent that the central turn or turns 38 substantially close the lumen. For the passage of a guide wire through the coil 32, the latter can be twisted in an unwinding direction, which will have the effect of opening the turns and thereby opening the lumen 40 through the element 32. This can be achieved readily when the connecting element 32 is made of a shape memory material, such as Nitinol. Once deployed, the turns of the coil 32 will twist back to their non-biased condition so as to recreate the waist 36 and close the lumen 40.

In the embodiment of FIGS. 3 and 4, the waist 36 can act as the closure element to the lumen 40, although it is not excluded that additional closure features of the nature described below may be used.

Figure 5:
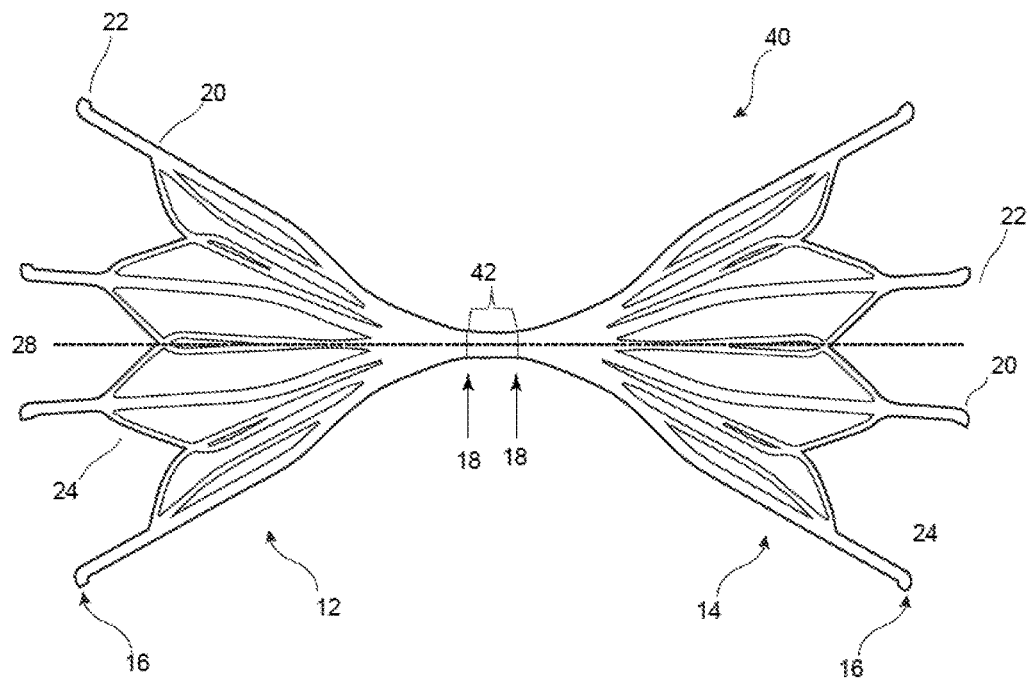
FIG. 5 is a schematic diagram in side elevation of another embodiment of filter.
Figure 6:
FIG. 6 is an enlarged view of a flexible connecting element in the form of a rod or cannula, for the filter of FIG. 5.

Referring now to FIGS. 5 and 6, these show another embodiment of implantable filter assembly 40 which has baskets 12, 14 similar to those of the embodiments of FIGS. 1 and 3 and which are coupled together at the narrow ends of the baskets by a flexible connecting element 42. The connecting element 42 may in some embodiments be a flexible rod formed, for example, from a polymer material or other material having elastic or even superelastic properties at the operating temperature of the device 40. Suitable materials include biocompatible polymers, alloys and also shape memory materials including for example Nitinol.

The connecting element 42 may likewise be a cannula having a lumen passing therethrough, so that the filter 10 may be deployed over a guide wire. In cases where the connecting element 42 is a cannula, there will also be provided a closure element of any of the types described below. A cannula may be made of the same material as a rod.

Figure 7:
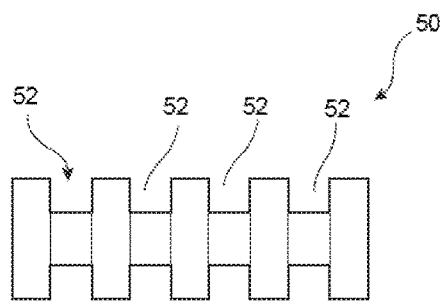
FIG. 7 is an enlarged view of an embodiment of grooved rod for use as the flexible connecting element for the medical device taught herein.

Referring now to FIG. 7, this shows another embodiment of connecting element 50, which in this example is a rod having a plurality of circumferentially extending grooves or recesses 52 arranged in series along the connecting element 50. The grooves 52 reduce the cross-section of the connecting element 50 and as a result increase its bending flexibility, that is in a direction normal to the longitudinal axis of the element 50. In the embodiment of FIG. 7, the grooves 52 are all the same size and extend for the whole length of the element 50. In other embodiments the grooves 52 could be of different sizes and/or may only be located along a part of the length of the element 50, for example around its centre point. The connecting element 50 may be made of any suitable flexible material such as steel, or shape memory material such as Nitinol. Other suitable materials include platinum, palladium and similar inert materials which have the advantage of being radiopaque.

Figure 8:
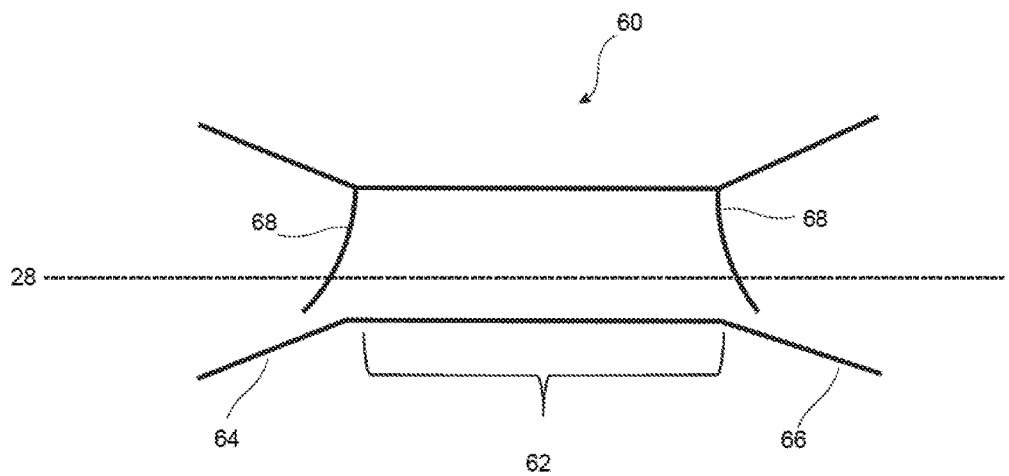
FIG. 8 is a schematic diagram of a filter as disclosed herein, provided with first and second valves.
Figure 9:
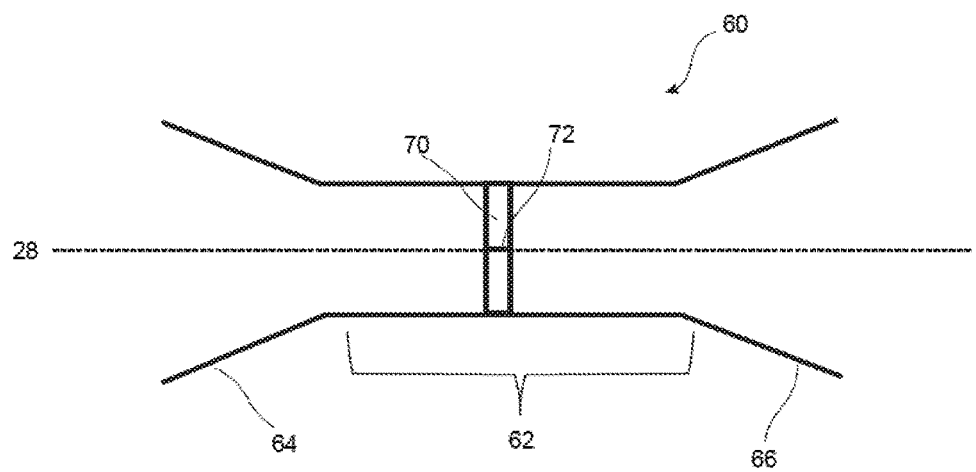
FIG. 9 is a schematic diagram of a filter as disclosed herein, provided with an internal cannula or coil valve element.
Figure 10:
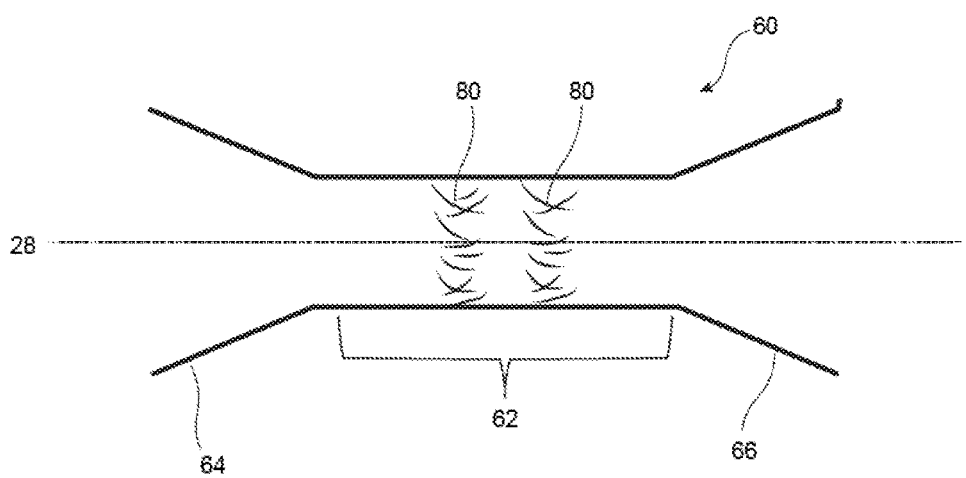
FIG. 10 is a schematic diagram of a filter as disclosed herein, provided with a bundle of thrombogenic fibres within the coil or cannula.

FIGS. 8 to 10 show in schematic form the filter assemblies of FIGS. 1, 3 and 5 with different arrangements of closure elements provided to close the lumen through the flexible connecting member. FIGS. 8 to 10 show only part of a filter assembly and in particular an enlarged portion of the flexible connecting element. Referring first to FIG. 8, the assembly 16 includes a flexible connecting element 62 which is integrally coupled to material capture elements 64, 66, of which only a portion can be seen in the Figure. The flexible connecting element 62, which may be any of the above-described forms, has a lumen 28 passing therethrough. Extending across the lumen and at each end of the connector element 62 is a valve 68, in this example being a radially flexible flap valve connected at one end or part of one edge to the connector element 62 or otherwise to a part of the frame structure 64, 66. Each valve element 68 has a natural unbiased position closing the lumen 28, that is the valve is able to be deflected to an open position (each valve 68 is shown partially open in FIG. 8) to allow the passage of a guide wire therethrough.

The skilled person will appreciate that a single valve element 68 may be provided, but it is preferred that two valve elements of this nature are used at the two ends of the connecting element 62, so that the assembly can be fitted within a patient's vessel in either orientation while still maintaining a closed lumen 28 after deployment of the device. The valve element 68 can be made of any suitable material, including silicone, Nylon, PET, PTFE and so on. Any suitable implant grade polymer could be used.

FIG. 9 shows another embodiment, in which there is provided within the lumen of the flexible connector 62 a valve element 60, which may be a disk vale having a slit 72 therein. The valve 70 can be opened by pushing a guide wire through the slit 72 and will then close again by its own resiliency once the guide wire has been removed. The valve element 70 can be made of any suitable known material.

FIG. 10 shows another embodiment, in which there is provided one or more sets of thrombogenic fibres 80 within the lumen 28 of the flexible connector element 62. The thrombogenic fibres 80 can be adhered or bonded to the flexible connecter element 62. Where the connector element 62 is formed from a coil the thrombogenic fibres can be wrapped around turns of the coil so as to be held thereby.

Figure 11:
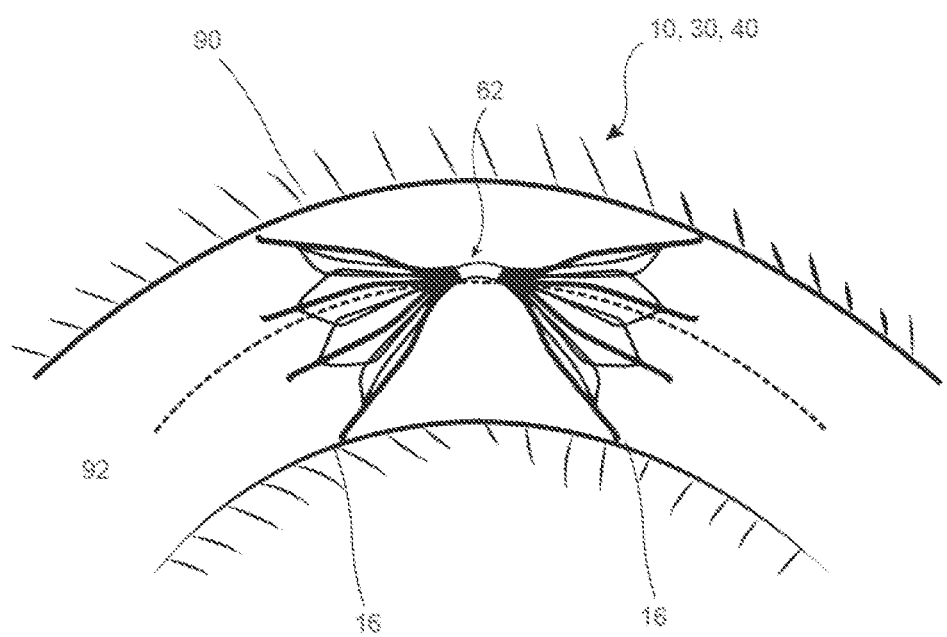
FIG. 11 shows an example of the device taught herein implanted in a curved vessel.

Referring now to FIG. 11, this shows the implantable medical device 10, 30, 40 within a blood vessel 90 of a patient and in particular at a point of curvature of the vessel 90. The wide ends 16 of the filter device engage with the vessel walls and are generally disposed perpendicular to the axis 92 of the vessel, thereby ensuring patency to the vessel wall and that there are no leaks of blood around the edges of the material capture elements of the device. This is achievable as a result of the flexible connector element 62 which, as can be seen in FIG. 11, can curve with the curvature of the lumen. As explained above, it is preferred that the resistance to curvature of the flexible connector element 62 is substantially less than the strength of the vessel 90 so as not to impart a great straightening force on the vessel. The device, therefore, has the advantage of a double ended medical device, such as a double ended filter or occluder, but without the disadvantage of known devices of this type.

It is to be appreciated that the entirety of the frame of the structure forming the implantable medical device may be made of a shape memory material such as Nitinol, that is the material capture elements as well as the connecting element. In other embodiments, the elements of the structure could be made of a spring material such as spring steel or the like. Any combination of materials could be used for the different parts of the structure, for instance a first material for the material capture elements and a different material for the connecting element.

It is to be understood that although the embodiments described above use a single closure element or type of closure element, the disclosure herein also encompasses embodiments having a plurality of different closure elements for a single device. One example would provide a combination of a valve and thrombogenic fibres.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in the abstract accompanying this application are incorporated herein by reference.

The invention claimed is:

1. An implantable medical device comprising:
    a first material capture element and a second material capture element, each material capture element having a wide end and a narrow end, the first and second material capture elements being disposed with their narrow ends facing one another and their wide ends extending in opposing directions;
    a flexible connecting element connected to the narrow ends of the first and second material capture elements to form a unitary device with the first and second material capture elements;
    the flexible connecting element being closable to passage of fluid therethrough;
    wherein the flexible connecting element has a biased condition and a non-biased condition, the flexible connecting element being in the shape of a coil when in both the biased condition and the non-biased condition, the coil providing a lumen passing there through, such that there is a continuous and uninterrupted channel passing through the centre of the medical device through which a fluid can flow when the coil is in the biased condition, there being provided a closure element to close passage of the fluid through the coil when the coil is in the non-biased condition.

2. The implantable medical device according to claim 1, wherein the connecting element comprises a coiled wire.

3. The implantable medical device according to claim 1, wherein the connecting element comprises a helically cut cannula.

4. The implantable medical device according to claim 1, wherein the closure element is disposed within the lumen of the coil.

5. The implantable medical device according to claim 1, wherein the closure element is disposed in one of the first and second material capture elements.

6. The implantable medical device according to claim 5 comprising a second closure element disposed in the other of the first and second material capture elements.

7. The implantable medical device according to claim 1, wherein the closure element comprises a portion of the coil comprising a narrow waist closing.

8. The implantable medical device according to claim 7, wherein the waist is openable by twisting, the closure element comprising a valve allowing passage through the lumen when open and blocking passage through the lumen when closed.

9. The implantable medical device according to claim 1, wherein the first and second material capture elements each comprise a frame, the connecting element being attached to each frame.

10. The implantable medical device according to claim 9, wherein the frames of the first and second material capture elements are one piece with the connecting element.

11. The implantable medical device according to claim 9, wherein the frames of the first and second material capture elements and the connecting element comprise a shape memory alloy.

12. The implantable medical device according to claim 1, wherein the device is an occluder and the material capture elements are impervious to fluid.

13. The implantable medical device according to claim 1, wherein the device is a filter and the material capture elements are fluid porous.

* * * * *